United States Patent [19]

Young

[11] Patent Number: 4,931,061
[45] Date of Patent: Jun. 5, 1990

[54] PLANT SEED COMPOSITIONS

[75] Inventor: Donald C. Young, Fullerton, Calif.

[73] Assignee: Union Oil Company of California, Brea, Calif.

[21] Appl. No.: 329,840

[22] Filed: Mar. 28, 1989

Related U.S. Application Data

[60] Division of Ser. No. 445,317, Jan. 3, 1983, Pat. No. 4,834,788, which is a continuation-in-part of Ser. No. 442,296, Nov. 17, 1982, abandoned, and a continuation-in-part of Ser. No. 444,667, Nov. 26, 1982, abandoned.

[51] Int. Cl.$^5$ ............................................... A01C 1/00
[52] U.S. Cl. ......................................... 47/57.6; 71/83
[58] Field of Search ............................. 47/57.6; 71/83

[56] References Cited

U.S. PATENT DOCUMENTS

| Re. 1,995 | 6/1865 | Hoffman | 127/36 |
|---|---|---|---|
| 1,340,708 | 5/1920 | Fjellanger | 71/28 |
| 1,878,852 | 9/1932 | Hoppler . | |
| 1,917,539 | 8/1933 | Miles . | |
| 1,919,623 | 8/1933 | Dreyfus . | |
| 2,767,108 | 10/1956 | Fetzer | 127/34 |
| 2,978,359 | 4/1961 | Wedell | 117/138.8 |
| 3,432,482 | 3/1969 | Ohfuka et al. | 260/85.5 |
| 3,558,530 | 1/1971 | Schroeder et al. | 260/2.5 |
| 3,660,070 | 5/1972 | Maruta et al. | 71/28 |
| 3,778,431 | 12/1973 | Knightlinger | 260/233.3 R |
| 3,816,375 | 6/1974 | Bozer et al. | 260/67 FA |
| 3,873,734 | 3/1975 | Higgins et al. | 426/69 |
| 3,878,304 | 5/1975 | Moore | 426/69 |
| 3,918,952 | 11/1975 | Neumiller | 71/28 |
| 4,116,664 | 9/1978 | Jones | 71/29 |
| 4,214,888 | 10/1981 | Young | 71/28 |
| 4,310,343 | 1/1982 | Verdegaal et al. | 71/28 |
| 4,315,763 | 2/1982 | Stoller et al. | 71/29 |
| 4,397,675 | 8/1983 | Young | 71/28 |
| 4,402,852 | 9/1983 | Young | 252/182 |
| 4,404,116 | 9/1983 | Young | 252/182 |
| 4,439,348 | 3/1984 | Akerberg | 252/426 |
| 4,445,925 | 5/1984 | Young | 71/28 |
| 4,447,253 | 5/1984 | Young | 71/28 |
| 4,451,577 | 5/1984 | Coss | 502/167 |
| 4,474,925 | 10/1984 | Sartoretto et al. | 71/119 |
| 4,512,813 | 4/1985 | Young | 134/27 |
| 4,522,644 | 6/1985 | Young | 71/78 |
| 4,589,925 | 5/1986 | Young | 134/3 |
| 4,626,417 | 12/1986 | Young | 423/235 |
| 4,664,717 | 5/1987 | Young | 127/37 |
| 4,673,522 | 6/1987 | Young | 252/87 |
| 4,686,017 | 8/1987 | Young | 204/45.1 |
| 4,722,986 | 2/1988 | Young | 527/203 |
| 4,743,669 | 5/1988 | Young | 527/200 |
| 4,755,265 | 7/1988 | Young | 204/45.1 |

OTHER PUBLICATIONS

Science News, vol. 123, No. 23, Jun. 4, 1983, p. 366; Science Service, Inc. 1719 N. Street, N.W., Washington, D.C., "Cellulose Digestion" by Lab Bacteria.
The Condensed Chemical Dictionary, Seventh Edition, Van Nostrand Reinhold Co., New York, 1969, p. 908.
D. F. duToit, Verslag Akad. Wetenschappen, 22 5/3-4 (abstracted in Chemical Abstracts, 8, 2346, (1914)).
L. H. Dalman, "Ternary Systems of Urea and Acids. I. Urea, Nitric Acid and Water. II. Urea, Sulfuric Acid and Water. III. Urea, Oxalic Acid and Water"; JACS 56, 549-553 (1934).
Sulfur Institute Bulletin No. 10 (1964), "Adding Plant Nutrient Sulfur to Fertilizer".
Kirk-Othmer Encyclopedia of Chemical Technology, Third Edition, John Wiley and Sons, New York, 1980, vol. 5, pp. 31-33 and 55-61; vol. 9, pp. 291-374; vol. 11, pp. 295-300, 662-665 and 694-695; and vol. 12, pp. 852-857 and 867-869.
"Organic Chemistry of Bivalent Sulfur," Chemical Publishing Co., 1962, pp. 14, 15, 94 and 95.
"The Chemistry of Carboxylic Acids and Esters," Interscience Publishers, 1969, pp. 732-759.
Title 40, Code of Federal Regulations, Section 180,1019, "Sulfuric Acid; Exemption from the Requirement of Tolerance."
Adalla, "Effects of Herbicidal Weed Control on Growth and Development of Ground Nuts (Arachis Hypogaea I.) in Western Kenya," Proceedings of the East African Weed Science Conference, 6, 1976, published 1977; Chemical Abstract, 93, 93:90069b, 1980 (Only the abstract is cited.).
Bach et al., Destroying Potato Plants, East German Patent 146,541, Feb. 18, 1981, Chemical Abst., 95, 95:37118g (1981) (Only the abstract is cited.).
Chen, Incidental Uses of Fertilizers, Urea and Muriate (List continued on next page.)

Primary Examiner—Glennon H. Hollrah
Assistant Examiner—E. Kraus
Attorney, Agent, or Firm—Gregory F. Wirzbicki; Michael H. Laird

[57] ABSTRACT

Plant seeds are beneficiated by contacting them with an aqueous solution of a urea-sulfuric acid component containing the monourea adduct of sulfuric acid. The molar ratio of urea to sulfuric acid in the aqueous solution is preferably within the range of about ¼ to about 7/4 so that at least about 25 percent of the sulfuric acid is present in the solution as the monourea adduct. The treatment of plant seeds with the aqueous urea-sulfuric acid components is particularly useful for removing residual plant matter from plant seeds, scarifying and improving the germination of plant seeds, and improving the processability and digestibility of plant seeds. Improvements in processability result from softened seed hulls or husks, improved extractability of oil from oil-containing seeds, and improved quality of treated seeds for the manufacture of seed derived products, particularly for the manufacture of grain-derived products. Compositions which involve mixtures of plant seeds and the urea-sulfuric acid components are also provided.

12 Claims, No Drawings

OTHER PUBLICATIONS of Potash in Mature and Immature Oil Palm Plants; Some Preliminary Results, Int. Dev. Oil Palm Proceedings, Malaysian International Agricultural Oil Palm Conference, 1977.

Kamilova et al., The Sensitivity of Weeds and Cotton to the Herbicide Toluin in Dependence on the Form of Nitrogen Fertilizers Used, The Institute of Experimental Plant Biology of the Academy of Sciences, UZBEKH, SSR, TASHKENT [INEBR AS Uz SSR], AGROKHIMIYA, 5, 1980, pp. 124–127 (transl from Russian).

Jelks, "Treating Cellulosic Plant Matter," Chemical Abstract, 91:37800r (1979).

Clark, Chemical Abstract, 94:29037w (1981).

PLANT SEED COMPOSITIONS

OF THE INVENTION

1. Field of the Invention

This invention relates to the treatment of plant seeds and, to compositions for use in such methods, in particular, it relates to methods and compositions useful for cleaning, scarifying, and improving the germination rate processability of plant seeds.

2. Description of the Art

Seeds of essentially all varieties are often treated by one or more procedures to improve their quality and utility for a variety of uses such as storage, planting, oil-extraction, and subsequent processing for the manufacture of seed-derived products such as animal foods, including human foods. Although most seeds are treated after harvest, some are treated before harvest by the application of chemicals maturation or that facilitate harvesting or that promote maturation or that facilitate harvesting or accelerate germination.

Residual mineral and organic matter, particularly residual plant matter which is not an integral part of the seed husk or hull, is most often removed from seeds intended for storage or subsequent use. The presence of such residual organic matter interferes with handling apparatus and procedures, promotes spoilage through the growth of bacteria and fungus, fouls the extraction products from certain seeds such as oils from cotton seeds and the like, and can inhibit germination in seeds that are replanted.

Current procedures for the removal of residual plant matter and other organic and/or mineral matter from plant seeds include washing with water or other solutions, mechanical abrasion, and treatment at elevated temperatures with strong base such as calcium hydroxide, sodium hydroxide, and the like. Seeds that are intended for replanting are often treated to improve their germination rate, i.e., to reduce the time required for seed germination after planting. Current practices for increasing germination rate involve scarifying the seeds, by mechanically scraping or chemically treating the seed husk to increase its permeability to moisture. Treatment with strong base increases the permeability of the seed covering (which consists principally of cellulose and lignand) by partially dissolving or modifying the seed covering. Increased germination rate minimize disease or parasite infestation prior to germination and often facilitates better timing of crop emergence and maturation.

Similar mechanical and caustic treating procedures are employed to clean and/or beneficiate seeds prior to extraction of oil or other seed products. Such treatments reduce the amount of energy required to recover oil from seeds by compression and/or increase the rate at which such oils are extracted. Plant seeds also are processed to improve their value as food for domestic animals and for the manufacture of (1) processed foods such as processed rice, wheat and other grains, (2) foods that require less cooking time for their preparation, (3) other seed-derived food products such as cereals, bakery products, flour, corn meal, etc., and (4) certain seed-derived vegetable products such as corn syrup, and soy bean meal and other vegetable protein concentrates.

Contemporary mechanical seed-treating methods such as mechanical scarification involve the use of relatively complicated equipment and the expenditure of mechanical energy. They do not always result in equal or homogeneous scarification and/or cleaning of all seeds and thus can produce a heterogeneous product. Furthermore, the necessity for complex mechanical equipment requires that the raw seeds be shipped to a location at which such equipment is available. The chemical treating methods such as hot caustic treatment involve the use of substantial amounts of caustic reactants which are often consumed in the process. Such methods also require elevated temperatures, and thus excessive energy input, and relatively long contact times.

It is known that sulfuric acid will chemically react with vegetable matter. However, sulfuric acid is such a strong oxidizing and sulfonating agent that it cannot be employed for seed treatment without also oxidizing and/or sulfonating desirable portions of the seed product.

Combinations of urea and sulfuric acid are also known and have been used in the agricultural industry primarily when the simultaneous addition of urea and sulfur to the soil is desired. It is also known that urea and sulfuric acid will combine to form adducts including the monourea-sulfuric acid adduct and the diurea-sulfuric acid adduct. For instance, D. F. du Toit, Verslag Akad. Wetenschsppen, 22, 573-4 (abstracted in Chemical Abstracts, 8, 2346, 1914) disclosed that urea forms certain compounds with oxalic, acetic hydrochloric, nitric and sulfuric acids. L. H. Dalman, "Ternary Systems of Urea and Acid. I. Urea, Nitric Acid and Water. II. Urea, Sulfuric Acid and Water. III. Urea, Oxalic Acid and Water"; JACS, 56, 549-53 (1934), disclosed the phase relationships between the solid phase and saturated solutions containing urea and sulfuric acid at 10° C. and 25° C. The Sulfur Institute, Sulfur Institute Bulletin No. 10 (1964), "Adding Plant Nutrient Sulfur to Fertilizer", disclosed that urea reacts with sulfuric acid to form two complexes of "urea sulfate" which are useful fertilizers. Methods of manufacturing certain combinations of urea and sulfuric acid are disclosed by Verdegaal et al. in U.S. Pat. No. 4,310,343 and by Jones in U.S. Pat. No. 4,116,664. However, neither these nor other investigators recognized that urea-sulfuric acid compositions containing a significant proportion of the monourea adduct of sulfuric acid are uniquely active toward organic materials such as residual organic matter contained on plant seeds and the husks or hulls of the plant seeds, or that the diurea adduct of sulfuric acid exhibits little, if any, of such activity.

Accordingly, a need exists for improved processes for treating plant seeds, and particularly for improved processes for cleaning and/or scarifying plant seeds, for increasing the germination rate of plant seeds, and for improving the quality of plant seeds for use in the manufacture of seed-derived products such as vegetable oils, vegetable protein concentrates, and food products.

It is therefore a principal object of this invention to provide novel methods for treating plant seeds.

Another object of this invention is the provision of methods for cleaning plant seeds.

Yet another object of this invention is the provision of methods for scarifying seeds.

Another object is the provision of methods for increasing the germination rate of plant seeds.

Yet another object of this invention is the provision of methods for improving the storage-stability of plant seeds.

Yet another object of this invention is the provision of methods for improving the quality of plant seeds for the manufacture of seed-derived products.

Another object is a provision of methods for improving the oil-extractability of oil-containing plant seeds.

Yet another object is the provision of methods for improving the processability of plant seeds for the manufacture of food products.

Another object is the provision of methods of extracting oil from oil-containing plant seeds.

Yet another object of the provision of novel seedcontaining compositions.

Another object is the provision of seed-containing compositions suitable for use in the manufacture of improved plant seeds.

Yet another object is the provision containing compositions suitable for use in the manufacture of seederived products such as vegetable oil and food products.

Other objects, aspects and advantages of this invention will be apparent to one skilled in the art in view of the following disclosure, the drawing and the appended claims.

SUMMARY OF THE INVENTION

Briefly, the invention provides (1) methods for treating plant seeds, (2) seed-containing compositions useful in such methods, and (3) methods of producing plant seed-derived products such as vegetable oils, vegetable protein concentrates, and other food products.

The novel methods of this invention involve contacting plant seeds with an aqueous solution containing urea and sulfuric acid, and optionally, a surfactant, in which solution the molar ratio of urea to sulfuric acid is within the range of about $\frac{1}{4}$ to about 7/4. Within this range of molar ratios, at least about 25 percent of the sulfuric acid present in the solution is in the form of the monourea adduct of sulfuric acid. The monourea-sulfuric acid adduct is the component of the urea-sulfuric acid solutions which is most active for the treatment of plant seeds. The methods of this invention enable the accomplishment of one or more of a variety of objectives depending upon the types of plant seed treated, the condition of the plant seed before treatment, and the treating conditions, the most important of which are the concentration and dosage rate of the urea-sulfuric acid solution, and treatment temperatures and contact times. For instance, seeds can be cleaned of residual matter which is not an integral part of the seed or seed husk or hull under relatively mild treatment conditions while more severe conditions are required to significantly change the thickness or permeability of the seed husk or hull. In contrast, the seed husk or hull can be partially or completely removed by the use of more severe treatment conditions including higher dosage rates of the active monourea-sulfuric acid adduct, higher contacting temperatures, and longer contact times. Thus, the methods of this invention can be employed to (1) clean plant seeds of residual organic and/or mineral matter including residual plant matter, (2) scarify or otherwise reduce the thickness of and/or increase the moisture permeability of the seed hull or husk, (3) increase seed germination rate, (4) improve seed storageability and resistance to bacterial and fungus infestation, (5) significantly reduce the thickness and physical strength of the seed hull or husk and/or (6) partially hydrolyze the seed hull, husk or the seed itself, and thereby improve the processability of the seeds for the manufacture of seed-derived products such as vegetable oils, animal foods, and food products. The methods of this invention are particularly useful for the removal of residual plant matter from raw seeds, such as the removal of lint from cotton seeds, and for improving seed germination rate and processability for the manufacture of products derived from seeds of essentially all plant varieties. These methods are also particularly useful for the beneficiation of seeds which have relatively hard, impervious husks or hulls.

The novel compositions of this invention involve mixtures of plant seeds and the urea-sulfuric acid components useful in the methods of this invention, which may optionally contain a surfactant. These mixtures usually involve combinations of aqueous solutions of urea and sulfuric acid in which the molar ratio of urea to sulfuric acid is within the range of about $\frac{1}{4}$ to about 7/4 dispersed over the seed's outer surface or in which the seeds to be treated are immersed. The urea and sulfuric acid, in combination, constitute at least about 0.5 weight percent of the novel compositions of this invention based on the weight of the treated plant seeds.

The methods and compositions of this invention minimize or eliminate many of the deficiencies associated with seed-treating processes presently available to the art. The described methods and compositions eliminate the need for complicated mechanical equipment such as that presently employed to clean, scarify and/or otherwise convert plant seeds for subsequent processing. They also eliminate need for the use of severe caustic treating processes and the relatively high energy demands associated with such processes. The urea-sulfuric acid components employed in the methods and compositions of this invention are relatively non-corrosive to both equipment and human skin and thus, are more easily handled than are caustics or sulfuric acid. Furthermore, the urea-sulfuric acid components, do not degrade desirable portions of the plant seed; such degradation almost unavoidably occurs from the use of sulfuric acid. These methods and compositions do not result in the addition of any toxic components to plant seeds and thus do not introduce toxic materials into seed-derived products. On the contrary, the urea-sulfuric acid components can be neutralized with base following contacting with the plant seeds to form compositions that contain nutrient nitrogen (from urea) and nutrient sulfur (from sulfuric acid), both of which are beneficial to seed-derived products such as animal feeds. Since the preferred urea-sulfuric acid components employed in this invention do not contain decomposition products of urea and/or sulfuric acid, such as sulfamic acid and ammonium sulfamate, they do not introduce such toxic materials into the seeds or into vegetable oils, food products, or other seed-derived products produced from the treated seeds.

DETAILED DESCRIPTION OF THE INVENTION

This invention provides novel methods for (1) cleaning and otherwise removing residual organic and inorganic matter from plant seeds, (2) scarifying plant seeds by reducing the thickness and increasing the moisture permeability of the seed hull or husk, (3) increasing the germination rate of plant seeds, (4) improving seed storage-stability and resistance to bacteria and fungus, and (5) improving the processing characteristics of plant seeds which are to be used for the manufacture of seed-derived products including vegetable oils, vegetable protein concentrates, starches, sugars, and fruit products, by at least partially hydrolyzing the hull and/or seed. Novel seed-containing compositions which are particularly useful in the methods of this invention are also provided.

The seed-treating methods of this invention involve contacting plant seeds with a urea-sulfuric acid component which preferably comprises an aqueous solution of urea and sulfuric acid in which the molar ratio of urea to sulfuric acid is within the range of about ¼ to about 7/4. The urea-sulfuric acid components contain an active amount of the monourea adduct of sulfuric acid and, within the range of molar ratios referred to above, at least about 25 percent of the sulfuric acid is present as the monourea-sulfuric acid adduct. The urea-sulfuric acid components may contain any one of a variety of other materials and, in particular, they may contain a surfactant. Surfactants increase the activity of the urea-sulfuric acid component toward seeds and other plant materials that contain lipophilic components such as fats, oils, waxes and other hydrophobic substances.

The novel seed-containing compositions of this invention involve mixtures of plant seeds and the urea-sulfuric acid components useful in the methods of this invention, with or without a surfactant. Such seed-containing compositions usually contain an amount of the urea-sulfuric acid component such that the urea and sulfuric acid, in combination, constitute at least about 0.5 weight percent of the composition.

Plant seeds which may be treated in accordance with the methods of this invention and/or which may constitute components of the novel seed-containing compositions of this invention include seeds of all seed-producing plants including all perennial and annual, coniferous and deciduous plants including trees, shrubs, vines, and grasses. The methods and compositions of this invention are particularly useful for the treatment of the seeds of such plants which are employed for ornamental, fruit-bearing, fiber producing and vegetable producing purposes, in addition to food and ornamental grasses, and of plants such as certain varieties of sunflower and cotton, the seeds of which are used in the production of oil and other seed-derived products. Illustrative food crops include grain crops such as wheat, barley, oats, corn, rice, and the like; vegetables such as carrots, lettuce, celery, artichokes and all varieties of peas, beans, and the like; and fruit crops such as berries, including blackberries, boysenberries, etc., cherries, avocadoes, pears, apples, citrus, etc. Illustrative grass crops include the various varieties of grass grown for hay including bermuda grass and alfalfa, and ornamental grasses such as Kentucky bluegrass, ryegrass, and the like. Illustrative of other ornamental plants are flowering plants such as azaleas, chrysanthemums, marigolds, and decorative vines such as mock strawberry and iceplant. Illustrative oil-producing plant seeds are the seeds of plants from which oils useful in foods or other products can be derived. Such products include food products, cooking oils, components of varnishes, soaps, drying oils for paints, waxy oils for waterproofing paper, and the like. Such seed oils are usually derived by expression (pressing) or solvent extraction of the raw or partially processed seeds of plants such as Helianthus annus (sunflower oil); safflower (carthamus) seeds which produce safflower oil; flax seed (Linum usitatissimum) from which linseed (flax seed) oil is derived; cotton; peanuts; perilla ocimaides from which perilla oil, a substitute for linseed oil, can be derived; seeds of the oiticica tree (Licania rigida) from which oiticica oil is derived; and seeds of Aleurites cordata used to produce Tung oil; and others.

The urea-sulfuric acid components employed in the methods and compositions of this invention are reaction products of urea and sulfuric acid in which the molar ratio of urea to sulfuric acid is within the range of about ¼ to about 7/4. In such components, at least about 25 percent of the sulfuric acid is present as the monourea-sulfuric acid adduct. These components may be employed in the methods disclosed herein, as melts or as solutions of such mixtures in water or other solvents, and they may contain other components such as surfactants which do not substantially negate the activity of the urea-sulfuric acid component.

The urea-sulfuric acid components may also contain unreacted (free) sulfuric acid or the diurea adduct of sulfuric acid. The useful and preferred proportions of urea, sulfuric acid, and of the mono- and diurea adducts of sulfuric acid, relative to each other, can be conveniently expressed in terms of the urea/sulfuric acid molar ratio. This ratio will usually be within the range of about ¼ to about 7/4, preferably about ½ to about 3/2, and most preferably between about 1/1 to about 3/2. Urea/sulfuric acid molar ratios within the range of about ¼ to about 7/4 define compositions in which at least 25 percent of the sulfuric acid is present as the monourea sulfuric acid adduct. Molar ratios within the range of ½ to about 3/2 define compositions in which at least 50 percent of the sulfuric acid is present as the monourea adduct. The most preferred molar ratio range of about 1/1 to about 3/2 defines compositions which contain essentially no uncomplexed sulfuric acid and in which at least 50 percent of the sulfuric acid is present as the monourea-sulfuric acid adduct. The most preferred combinations have urea/sulfuric acid molar ratios of about 1/1. In such compositions, essentially all of the sulfuric acid is present as the monourea-sulfuric acid adduct and such compositions are essentially free of uncomplexed sulfuric acid. Substantial amounts of uncomplexed sulfuric acid, i.e., sulfuric acid that is not complexed with urea as either the mono- or diurea adduct, are unpreferred since sulfuric acid, when present in substantial amounts, may promote reactions such as oxidation, sulfonation and/or other reactions. While excess urea is generally not detrimental to the performance of the urea-sulfuric acid components, the presence of excess urea above the amount required for a urea/sulfuric acid molar ratio of 1/1, results in the conversion of a portion of the monourea-sulfuric acid adduct to the diurea adduct which has little or no activity for beneficiating plant seeds in accordance with this invention. In fact, compositions in which a large percentage of the sulfuric acid is combined as the diurea adduct (such as 28-0-0-9 which contains only the diurea adduct and excess urea) can inhibit or even destroy the germinating ability of plant seeds. Thus, the preferred urea-sulfuric acid components are those in which at least about 75, usually at least about 85, and most preferably at least about 90 percent of the sulfuric acid is present as the mono- and/or diurea-sulfuric acid adduct. Particularly preferred compositions are those that contain essentially no free sulfuric acid; thus essentially 100 percent of the sulfuric acid would be combined with urea as the mono- and/or diurea adduct. Furthermore, since the monourea adduct is the most active combined form of urea and sulfuric acid, and since the diurea adduct is undesirable, at least in these embodiments of this invention in which preservation of the seed-germinating ability is desired, at least about 25, usually at least about 50, preferably at least about 70, and most preferably about 80 to about 100 percent of the sulfuric acid is present as the monourea-sulfuric acid adduct.

The urea-sulfuric acid components can be produced by the reaction of urea and sulfuric acid and, optionally water, by either batch or continuous processes. The more concentrated solutions, i.e., those containing less than 25 weight percent, preferably less than 15 weight percent water, are particularly preferred for purposes of manufacture, storage and shipment. Also, the urea-sulfuric acid component is preferably substantially or completely free of decomposition products of urea and/or sulfuric acid such as sulfamic acid, ammonium sulfamate, ammonium sulfate, etc., to assure that the preferred liquid and solid urea-sulfuric acid components employed in the methods and compositions of this invention are also free of such decomposition products. The absence of decomposition products in the urea-sulfuric acid component also assures that the sulfuric acid activity of that component has not been degraded by decomposition. Sulfuric acid decomposition also reduces the amount of acid in the urea-sulfuric acid component available to combine with the urea to form the active monourea-sulfuric acid adduct.

Urea-sulfuric acid components free of decomposition products can be produced by the reaction of solid urea and concentrated sulfuric acid by the methods described in my copending application Ser. No. 318,629 filed Nov. 5, 1981, now U.S. Pat. No. 4,445,925 the disclosure of which is incorporated herein by reference.

Solid urea-sulfuric acid components useful in producing the solutions employed in the methods of this invention can be obtained by crystallization from their respective aqueous solutions, as described in my copending application Ser. No. 444,667, "Methods for Controlling Vegetation", filed Nov. 26, 1982, the disclosure of which is incorporated herein by reference. Surfactants or other components, when present, will either crystallize at approximately the same temperature as the urea-sulfuric acid component or will be entrained with the crystallized urea-sulfuric acid component or will be entrained with the crystallized urea-sulfuric acid component. In the alternative, the surfactant and/or other components can be added, when desired, to the dry or damp urea-sulfuric acid component by any suitable mixing technique after crystallization of the urea-sulfuric acid component from its solution.

As described in my copending application Ser. No. 444,667, the urea-sulfuric acid aqueous solution there referred to as 18-0-0-17 has a crystallization temperature of 50° F. Designations such as 18-0-0-17 are conventionally used in the agricultural industry to define the weight percentages of nitrogen, phosphorus, potassium and a fourth component, in this case sulfur, contained in a composition. Thus, 18-0-0-17 contains 18 weight percent nitrogen as urea, 0 percent phosphorus, 0 percent potassium, and 17 weight percent sulfur. The 18-0-0-17 solution has a urea/sulfuric acid molar ratio of about 1.2 and contains about 90 weight percent of a combination of urea and sulfuric acid. Urea and sulfuric acid, in combination, constitute 80 weight percent of the aqueous solution designated as 10-0-0-19 in copending application Ser. No. 444,667, which composition has a urea/sulfuric acid molar ratio of about 0.6 and which crystallizes at about 42° F. The aqueous solution designated as 9-0-0-25 comprises approximately 96 weight percent of a combination of urea and sulfuric acid, has a urea/sulfuric acid molar ratio of about 0.4, and crystallizes at 14° F. The indicated crystallization temperatures of the three urea-sulfuric acid aqueous solutions referred to immediately above, and the crystallization temperatures for other formulations of urea and sulfuric acid useful in the composition and methods of this invention, are illustrated, in part, by the isotherms in the ternary phase diagram for urea, sulfuric acid and water in the drawing accompanying copending application Ser. No. 444,667. The crystallization temperatures for other urea-sulfuric acid combinations useful in the compositions and method of this invention can be determined from that drawing or by cooling the selected solution until crystallization occurs. The crystallized material can be separated from the supernant aqueous phase by any suitable solid-liquid separation technique such as filtration, centrifugation, decanting, and the like, and the recovered damp solid can be dried by evaporation if desired.

The aqueous solutions of the urea-sulfuric components useful in the treatment of seeds in accordance with methods and compositions of this invention can be either concentrated or very dilute. Although the monourea adduct appears to dissociate to urea and sulfuric acid in solutions containing significantly less than about 0.5 weight percent combined urea and sulfuric acid, the dissociated components can recombine to form the active adduct on the treated seeds if water is allowed to evaporate.

However, very low urea-sulfuric acid component concentrations, e.g., 0.2 percent, or less, generally do not allow for sufficient dosage rates of the active urea-sulfuric acid component in many instances. Thus, urea and sulfuric acid, in combination, will usually constitute at least about 0.5, generally at least about 1, preferably at least about 5, and the most preferably at least about 10 weight percent of the aqueous solutions as applied to the seeds. Aqueous solutions containing higher concentrations of the useful urea-sulfuric acid components, while more active, are also more viscous and are more difficult to apply evenly to the treated seeds. With these factors in mind, the applied solution will usually contain about 0.5 to about 90, normally about 1 to about 90, and preferably about 5 to about 80 weight percent urea and sulfuric acid on a combined weight basis.

The urea-sulfuric acid component-containing compositions employed in the methods of this invention may also contain one or more surfactants. Surfactants increase the activity of the urea-sulfuric acid component toward plant seeds, particularly toward seeds that contain and/or are combined with lipophilic substances such as waxes, oils and other hydrophobic substances. Surfactants also increase the wetting ability of the aqueous solutions useful in this invention and, thereby, improve the distribution of such solutions over the seed surface.

The selected surfactant is preferably sufficiently chemically stable in the presence of the urea-sulfuric acid component to assure that the surfactant retains its wetting ability for the period of time required to manufacture, store, transport, and apply the composition. The stability of any surfactant can be readily determined by adding an amount of the surfactant to the urea-sulfuric acid component-containing composition in which it is to be employed, and monitoring the combination by conventional nuclear magnetic resonance (NMR) techniques. NMR can be used to monitor the frequency and magnitude of spectral peaks characteristic of a selected nucleus, e.g., a hydrogen nucleus, in the subject molecule, i.e., in the surfactant. Persistent spectral peak magnitude and frequency over a period of 5 to 6 hours indicate stability. Diminished magnitude or a shift in peak frequency associated with the selected nucleus indicates instability, i.e., that the arrangement of functional groups in the surfactant molecule has been modified.

Illustrative of classes of stable surfactants are nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

The surfactant concentration is preferably sufficient to increase the wetting ability of the aqueous solution for the plant seeds and will usually be at least about 0.05, generally at least about 0.1, and preferably at least about 0.2 weight percent of the aqueous solution as applied. Surfactant concentrations of about 0.2 to about 1 weight percent are adequate in most applications. The concentration of surfactant in the solid urea-sulfuric acid components which also can be employed in this invention should be sufficient to produce the desired concentration in the aqueous solution that is to be produced by dissolving the solid in water. For example, a solid urea-sulfuric acid component that is to be dissolved to produce an aqueous solution containing 5 weight percent of a combination of urea and sulfuric acid would be diluted by a factor of 19 to 1 in order to produce that solution. Thus, the solid component should contain approximately 19 times the surfactant concentration desired in the solution on a weight percent basis. Hence, if a surfactant concentration of 0.1 weight percent is desired in the final solution, the solid component should contain approximately 1.9 weight percent of the surfactant.

The solid and liquid urea-sulfuric acid-containing compositions useful in this invention may also contain other components such as food additives, solvents, plant seed processing aids such as organic solvents, plant nutrients, biocides, plant growth regulants, etc., which do not neutralize the sulfuric acid contained in the urea-sulfuric acid component, react with the urea-sulfuric acid component, or otherwise substantially inhibit the activity of the urea-sulfuric acid component toward the plant seeds.

The aqueous solutions employed in the methods of this invention can be produced by any method capable of mixing the desired components to produce a solution of the desired composition. Thus, the surfactant and/or other components, when used, can be added to the concentrated urea-sulfuric acid solution during or immediately after its manufacture by the process described in my copending application Ser. No. 318,624, referred to above, or they can be added the solution with the plant seeds to be treated. Alternatively, the optional components can be mixed with the amount of water required to produce a concentrated or dilute aqueous solution or concentrated aqueous urea-sulfuric acid component. Of course, dissolution of the solid compositions useful in this invention that contain both the urea-sulfuric acid component and the desired optional components, in water, will also result in formation of the active aqueous compositions of this invention.

The methods of this invention involve contacting the plant seeds to be treated with an aqueous solution of the urea-sulfuric acid component under conditions of time, temperature, and dosage rate sufficient to accomplish the desired degree of seed modification. The plant seeds can be contacted with the aqueous urea-sulfuric acid component by any one of several suitable methods which include spraying the seeds with the aqueous solutions, immersing the seeds in the solution, or dusting the seeds with the solid urea-sulfuric acid components and then contacting the mixture with sufficient water to form the aqueous solution in contact with the plant seeds. Of course, the seeds can be dampened prior to application of the solid urea-sulfuric acid component. After the desired degree of seed modification has been achieved, the seeds can be separated from the aqueous urea-sulfuric acid component by filtering (when the seeds are immersed in the described solutions) or by washing with water. Optionally, the urea-sulfuric acid component can be neutralized by mixing the treated plant seeds with an amount of base such as sodium hydroxide, calcium hydroxide, potassium hydroxide, etc., sufficient to neutralize the sulfuric acid contained in the urea-sulfuric acid component. The neutralized urea-sulfuric acid component can be retained as a component of the seed product or can be washed from the seeds with water.

The plant seeds to be treated can be contacted with the aqueous urea-sulfuric acid components either prior to or after harvest. Thus, the aqueous urea-sulfuric acid components can be sprayed onto unharvested seeds in situ on the plant and the seeds can then be harvested or can be allowed to drop in place as desired. The methods of this invention can also be employed to treat partially processed plant seeds such as seeds that have already been cleaned of residual organic matter, seeds which have been partially scarified by chemical or mechanical means, or which have been partially hydrolyzed by contact with caustic as described above.

The contacting temperatures employed in the methods of this invention should be above the crystallization point of the aqueous urea-sulfuric acid component and below its thermal decomposition temperature which is approximately 176° F. Thus, contacting temperatures will usually be within the range of about 32 to about 170° F., generally about 40 to about 160° F., preferably about 60 to about 160° F. Contacting temperatures of about 60 to about 90° F. are generally sufficient for most purposes. The rate at which seed modification occurs increases as contacting temperature is increased. Thus, the rate at which residual plant matter is removed and at which seeds are scarified and/or hydrolyzed, increases as contacting temperature is increased.

The plant seeds should be contacted with the aqueous urea-sulfuric acid components for a period of time sufficient to achieve the desired degree of modification. Contact times will usually be at least about 1 minute, generally at least about 5 minutes, and preferably at least about 10 minutes. Contact times in the range of about 1 minute to about 100 hours are sufficient to achieve essentially all degrees of seed modification desired. Nevertheless, since the urea-sulfuric acid components remain active indefinitely unless they are neutralized, contact times much longer than 100 hours may be employed if desired to achieve more complete conversion. The extent of seed modification, i.e., the extent of organic matter removal, scarification, and digestibility and processability improvement, increases as contact time is increased.

The dosage rate of the urea-sulfuric acid component may be varied over a wide range and should be sufficient to accomplish the desired degree of seed modification within the contact time and at the contact temperature employed. Generally, the amount of the aqueous solution applied should be sufficient to cover a significant portion or all of the seed surface or should be sufficient to allow immersion of the seeds in the aqueous solution when complete immersion is desired. The dosage rate of the urea-sulfuric acid component, expressed on a waterfree basis, will usually be at least about 0.5, usually at least about 1, and preferably at least about 5 pounds of the combination of urea and sulfuric acid per 100 pounds of treated seeds. When applied at these dosage rates, the urea and sulfuric acid, in combination, will constitute at least about 0.5, generally at least about 1 and preferably at least about 5 weight percent of the treated seeds.

Essentially all types of seed modification in accordance with this invention can be achieved at dosage rates within the range of about 0.5 to about 200 pounds of the combination of urea and sulfuric acid per 100 pounds of treated seeds. Of course, much higher dosage rates can be employed to facilitate complete immersion of the plant seeds, continuous processing, and the like. The rate at which seed modification occurs increases with dosage rate of the urea-sulfuric acid component up to the point that the plant seed surfaces are completely wet with the aqueous urea-sulfuric acid component. The rate at which seed modification occurs does not increase significantly past that point unless the seeds contain basic materials that neutralize a portion of the sulfuric acid in the urea-sulfuric acid component. In such instances, an excess of the urea-sulfuric acid component should be provided.

Contacting temperature, contact time, and dosage rate of the urea-sulfuric acid component can be correlated to achieve the desired degree of seed modification. Thus, the plant seeds can be rapidly modified by contacting them with a moderate dosage of the urea-sulfuric acid component, e.g., about 10 pounds of the combination of urea and sulfuric acid per 100 pounds of treated seeds, for a relatively short contact time of approximately 10 minutes, at an elevated temperature of 150° F. A similar degree of modification can be achieved at the same dosage rate by employing a contacting temperature of 70° F. and a longer contact time. The optimum combination of contact temperature, time, and dosage rate, can best be determined by treating separate samples of the plant seeds at different dosage rates, contact temperatures and times, observing the extent of seed modification which occurs in each test, and selecting the combination of processing conditions best suited to accomplish the desired degree of modification of the tested plant seeds.

Relatively mild contacting conditions are usually adequate to clean plant seeds of residual organic matter. Thus, lint can be removed from cotton seeds by treatment with sufficient 10-0-0-18 to completely wet the seeds at 70° F. within approximately 20 minutes. Longer contact times can be employed without damage to the treated cotton seeds. Such procedures can be employed to remove residual organic matter of any type from all varieties of plant seeds. Thus, residual fruit matter can be removed from fruit seeds such as peach pits, citrus seeds, grains and the like. The cleaning of plant seeds by the methods of this invention improves their handling characteristics and reduces the likelihood of spoilage during storage due to bacterial or fungus infestation.

Plant seeds can be scarified, and seed germination rate can be increased by contacting the seeds with the urea-sulfuric acid component under relatively mild conditions similar to those employed to remove residual organic matter as discussed above. Scarification involves physical or chemical weakening and/or partial removal of the seed husk or hull. Germination rate is improved by increasing the permeability of the seed husk or hull to moisture. Further improvements in both of these characteristics can be achieved by treating the plant seeds under somewhat more severe conditions, i.e., for longer contact times, at higher temperature and/or with higher dosage rates of the urea-sulfuric acid component. However, it is generally preferable to avoid completely penetrating and/or removing the seed husk or hull if the seeds are to be replanted, since even the scarified seed husk protects the seed against disease and parasites. Thus, the treatment conditions employed to improve the germination rate of plant seeds should not be so extreme that they destroy the seeds viability, i.e., its ability to germinate. Seed viability and the extent of improvement in germination rate can be determined by any one of several procedures known in the art. For instance, the germination rate and viability of seed samples treated under different conditions of time, temperature and/or dosage rate, can be readily evaluated by the so-called "wet towel" germination and viability test. In accordance with this test several treated seeds are placed on a moist paper or cloth towel and are maintained at a temperature of approximately 90° F. for a period of time sufficient to allow germination. The absence of germination indicates that seed viability has been impaired. In the alternative, samples of the seeds treated under different conditions can be planted, either in the greenhouse or in field plots, and the rate of seedling emergence can be observed and employed as an index of germination rate and viability. The treatment conditions required to obtain significant scarification and/or germination rate improvement of seeds that have relatively thick, tough husks and/or hulls are more severe than are the conditions required to achieve similar improvements with seeds that have thinner coverings. For instance, higher dosage rates, longer contact times, and/or higher contacting temperatures are required to effect a significant degree of scarification and/or germination rate improvement with fruit seeds such as peach and avocado seeds than are required for vegetable, grain and flowering plant seeds such as lettuce, wheat, barley, and ornamental flower seeds.

The methods of this invention can also be employed to improve the processability and/or the digestibility of plant seeds. In particular, these methods can be employed to soften the seed hull or husk or to completely remove such seed coverings and thereby simplify subsequent processing such as the extraction of oils from oil-containing seeds and the manufacture of food products for animals including humans.

The production of vegetable oils can be facilitated by contacting the oil-containing seeds with the urea-sulfuric acid component in accordance with this invention under conditions sufficient to substantially weaken or remove the seed covering. Such contacting conditions are generally more severe than those required to just remove residual organic matter (although the removal of such organic matter also facilitates and simplifies the recovery of oil from seeds). Illustrative of suitable contacting conditions are contact times of at least about 30 minutes, and contacting temperatures of at least about 90° F. Similar improvements in oil-extractibility can be achieved at lower temperatures and longer contact times, or, conversely, higher temperatures and shorter contact times. The seed-oil may then be produced by solvent extraction and/or expression procedures which are known in the art. Illustrative of vegetable oils the production of which can be facilitated by this invention are sunflower oil, safflower oil, linseed oil, cotton seed oil, peanut oil, perilla oil, oiticica oil, Tung oil, and the like.

The digestibility of plant seeds by all types of animals, including humans, can be improved by treating the plant seeds in accordance with the methods of this invention. Even very mild contacting conditions improve the digestibility of plant seeds to a detectable extent. Greater improvement in digestibility and food value can be achieved by the use of longer contact times, higher contacting temperatures, and/or higher dosage rates The methods of this invention are particularly suitable for improving the digestibility and food value of grains such as corn, wheat, rye, barley, and of plant seeds which are customarily used for the manufacture of animal feeds such as cottonseed which is employed to manufacture cotton seed meal for cattle and other domestic animals. Seeds which are to be employed in animal feeds can be treated, in accordance with this embodiment, either as the whole raw seed, or they can be crushed or subdivided by grinding or milling prior to treatment. Crushed or subdivided seeds have higher surface areas and at least partially weakened physical structure, both of which increase the rate at which the seed components can be converted to feeds of improved food value.

Significant improvement in food value can be achieved within the time frames referred to above. The extent of food value improvement can be determined by digestibility tests known to the food processing industries. For instance, the degree of improvement of ruminant food value can be determined by procedures known to the animal husbandry industry such as the artificial ruminant study which involves the determination of invitro dry matter disappearance (IVDMD) The invitro dry matter disappearance test involves the innoculation of standard nutrient broth containing the treated seeds with rumen microorganisms at standard pH and temperature for about 12 to 16 hours and determining, by filtration and drying, the amount of dry matter remaining in the digested mixture Comparison of that value to the amount of dry matter added to the nutrient broth establishes the extent to which the treated seeds have been digested Similar tests are available for determining the food value of human foods, and the results of such tests can be employed to provide at least a qualitative evaluation of food value for other animals as well.

These methods are also useful for improving the processability of plant seeds when it is desired to convert the plant seeds to seed-derived products, and they are particularly useful for the manufacture of grain products such as bakery products, flour and other baking materials, cereals and other grain-containing breakfast foods, fast-cooking rice, wheat and other grains, and other seed-derived products. These methods are also useful for improving the processability of plant seeds for the manufacture of secondary food products such as corn syrup, corn starch and starches derived from other grain crops, and the like. The rate at which the improvements in plant seed processability are achieved and, thus, the degree of improvement obtained with any particular combination of temperature, dosage rate and contact time, can be increased by crushing and/or subdividing the plant seeds prior to or during treatment.

The novel methods of this invention provide expedient procedure for removing residual organic material from plant seeds, scarifying or otherwise reducing the thickness of and/or increasing the moisture permeability of seed hulls or husks, increasing seed germination rate, improving seed storage-stability, and improving the processability of plant seeds for the manufacture of seed-derived products. As one dramatic demonstration of the advantages of this invention, cotton seeds covered with lint can be completely delinted, and their germination rate can be increased by as much as 20 percent, in a simple batch operation by immersing the seeds in the 17-0-0-17 formulation at ambient temperature for about one hour.

These methods do not require the use of complex mechanical equipment such as that required for conventional mechanical plant seed scarifying procedures. Nor do they require the use and expenditure of substantial quantities of caustic or other reactants. They also do not result in the introduction of any toxic materials into the treated plant seeds or seed-derived products. On the contrary, these methods introduce nutrient nitrogen and sulfur into the treated seed product, which components are useful feed supplements for some domestic animals The preferred urea-sulfuric acid components employed in the methods and compositions of this invention do not contain potentially toxic decomposition products of urea and/or sulfuric acid such as sulfamic acid or ammonium sulfamate and thus do not introduce those materials into the seed product or seed-derived products. The methods of this invention also provide the user with considerable flexibility in controlling the quality of the seed product depending upon the contacting temperatures, times and dosage rates employed. Thus, cotton seeds may be treated under conditions which are sufficient only to remove residual lint or, by the use of more severe contacting conditions, may be converted to a product that is more easily processed to obtain cotton seed oil and/or to produce cotton seed-derived food products such as cotton seed meal. Similar results can be achieved with other plant seeds.

The invention is further described by the following examples which are illustrative of specific modes of practicing the invention and are not intended as limiting the scope of the invention as defined by the appended claims.

EXAMPLE I

Cotton seeds, as received from a cotton gin still covered with lint, are contacted with a urea-sulfuric acid component having the composition 10-0-0-18 by immersing the seeds in the urea-sulfuric acid component for 40 minutes at 70° F. The treated cotton seeds are then removed from the solution and washed with water. The treated seeds are completely free of cotton lint and the surfaces of the seeds appear to be somewhat darkened toward brown, apparently due to the removal of a portion of the outer seed coating.

EXAMPLE II

The operation described in Example I is repeated with the exception that the lint-containing cotton seeds are treated by immersion in a urea-sulfuric acid component having the formulation 17-0-0-17 at 70° F. for one hour. The treated seeds recovered from the urea-sulfuric acid component are completely free of lint.

EXAMPLE III

The cotton seed treatment described in Example I is repeated with the exception that the lint-containing cotton seeds are treated by immersion in a urea-sulfuric acid mixture having the composition 28-0-0-9 for 3 hours at 70° F. Even after such contacting, very little, if any, of the lint is removed from the seeds.

EXAMPLE IV

Quantities of the untreated cotton seeds employed in Examples I, II, and III, and of the seeds treated in those examples are planted in potting mix and are maintained in a greenhouse at about 80° F. until germination occurs. The untreated cotton seeds germinate and the seedlings break through the soil surface in approximately 5 ½ days. The seeds treated in Examples I and II germinate, and essentially all of the seedlings break through the soil surface, at the same time in approximately 4 days. Only one seed treated in Example III, out of more than 50 which are planted, germinates and breaks through the soil surface in two weeks.

EXAMPLE V

Avocado seeds are scarified by immersing the seeds in urea-sulfuric acid component having the formulation 18-0-0-17 at 90° F. for 90 minutes.

EXAMPLE VI

The processability of sunflower seeds for the subsequent extraction of the sunflower seed oil is improved by spraying the seeds with a urea-sulfuric acid component having the formulation 10-0-0-18 at a dosage rate corresponding to 5 pounds of the combination of urea and sulfuric acid per 100 pounds of sunflower seeds and maintaining the coated seeds at 80° F. for 1 hour. The seeds are then washed with water and are processed by conventional methods to recover sunflower seed oil.

EXAMPLE VII

The processability of raw wheat for the production of wheat flour is improved by spraying the wheat seeds with a urea-sulfuric acid component having the composition 17-0-0-17 at a dosage rate corresponding to 10 pounds of the combination of urea and sulfuric acid per 100 pounds of raw wheat seeds. The wheat is contacted for 1 hour at 70° F., washed with water to remove the urea-sulfuric acid component and milled to produce wheat flour.

EXAMPLE VIII

The germination rate of rice is increased by spraying the rice seeds evenly with a urea-sulfuric acid component having the formulation 17-0-0-17 at a dosage rate corresponding to 4 pounds of the combination of urea and sulfuric acid per 100 pounds of rice seeds, mixing to assure even distribution of the urea-sulfuric acid component over the rice seeds, and contacting the resulting mixture for 20 minutes at 70° F. The treated rice seeds are water washed to remove the urea-sulfuric acid component.

EXAMPLE IX

The storage stability of peach seeds which have residual fruit matter on the seed hull is improved by spraying the peach seeds with an aqueous urea-sulfuric acid component prepared by diluting 1 volume of 17-0-0-17 with 4 volumes of water and applying the resulting solution evenly to the outer surfaces of the peach seeds at a dosage rate corresponding to 2 pounds of the combined weight of urea and sulfuric acid per 100 pounds of peach seeds. The treated seeds are stored without further treatment or are water washed to remove the urea-sulfuric acid component 1 hour after application.

While particular embodiments of this invention have been described, it will be understood, of course, that the invention is not limited thereto since many obvious modifications can be made and it is intended to include within this invention any such modifications as will fall within the scope of the appended claims.

Having described my invention, I claim:

1. A composition of matter comprising a mixture of plant seeds and an aqueous solution comprising urea and sulfuric acid, in which solution the molar ratio of said urea to said sulfuric acid is within the range of about ¼ to about 7/4, and wherein said urea and said sulfuric acid, in combination, constitute at least about 0.5 weight percent of said solution.

2. A composition of matter comprising a mixture of plant seeds and the monourea adduct of sulfuric acid.

3. A composition of matter comprising a mixture of plant seeds and the reaction product of urea and sulfuric acid, in which reaction product the molar ratio of said urea to said sulfuric acid is within the range of about ½ to about 3/2.

4. The composition defined in any one of claims 1, 2 or 3 further comprising a surfactant.

5. The composition defined in any one of claims 1, 2 or 3 free of decomposition products of urea and sulfuric acid.

6. The composition defined in any one of claims 1, 2 or 3 free of sulfamic acid and ammonium sulfamate.

7. The composition defined in any one of claims 1 or 3 wherein said molar ratio of urea to sulfuric acid is at least about 1.

8. The composition defined in any one of claims 1, 2 or 3 wherein the concentration of equivalent urea and sulfuric acid, in combination, corresponds to at least about 0.5 pound per 100 pounds of said seeds.

9. The composition defined in any one of claims 1, 2 or 3 wherein the concentration of equivalent urea and sulfuric acid, in combination, corresponds to at least about 1 pound per 100 pounds of said seeds.

10. The composition defined in any one of claims 1, 2 or 3 wherein the concentration of equivalent urea and sulfuric acid, in combination, constitutes at least about 5 pounds per 100 pounds of said seeds.

11. The composition defined in any one of claims 1, 2 or 3 free of sulfamic acid and ammonium sulfamate, wherein the concentration of equivalent urea and sulfuric acid, in combination corresponds to at least about 1 pound per 100 pounds of said seeds.

12. The composition defined in claim 11 further comprising a surfactant.

* * * * *